United States Patent [19]

Füller

[11] Patent Number: 4,732,753

[45] Date of Patent: Mar. 22, 1988

[54] SUPPOSITORY DOSAGE FORM

[75] Inventor: Walter Füller, Therwil, Switzerland

[73] Assignee: Hoffmann-La Roche Inc., Nutley, N.J.

[21] Appl. No.: 700,168

[22] Filed: Feb. 11, 1985

[30] Foreign Application Priority Data

Feb. 22, 1984 [CH] Switzerland .......................... 858/84

[51] Int. Cl.$^4$ .................. A61K 9/02; A61K 9/62; A61K 9/36

[52] U.S. Cl. .................. 424/85; 424/DIG. 15; 514/198; 514/199; 514/200; 514/206; 514/786; 514/965; 514/970

[58] Field of Search .................. 424/DIG. 15, 85; 514/786, 206, 965, 966, 970, 198, 199, 200

[56] References Cited

U.S. PATENT DOCUMENTS

| | | | |
|---|---|---|---|
| 4,156,719 | 5/1979 | Sezaki et al. | 514/786 |
| 4,327,210 | 4/1982 | Montavon et al. | 540/227 |
| 4,338,306 | 7/1982 | Kitao et al. | 514/4 |
| 4,347,237 | 8/1982 | Evenstad et al. | 424/DIG. 15 |
| 4,368,185 | 1/1983 | Mizuno et al. | 424/DIG. 15 |
| 4,462,984 | 7/1984 | Mizuno et al. | 514/786 |
| 4,485,033 | 11/1984 | Kitao et al. | 514/966 |
| 4,525,339 | 6/1985 | Behl et al. | 424/459 |

FOREIGN PATENT DOCUMENTS

| | | | |
|---|---|---|---|
| 58-213710 | 12/1983 | Japan | 424/DIG. 15 |
| 59-42317 | 3/1984 | Japan | 514/966 |
| 60-197618 | 10/1985 | Japan | 514/966 |

*Primary Examiner*—Ronald W. Griffin
*Attorney, Agent, or Firm*—Jon S. Saxe; Bernard S. Leon; Matthew Boxer

[57] ABSTRACT

Suppositories containing as the active substance a therapeutically effective amount of ceftriaxone, a pharmaceutically compatible salt thereof or a hydrate of one of these compounds, a stabilizer consisting of a mono-, di- or triglyceride of a $C_{12}$–$C_{18}$-fatty acid or of a mixture of such glycerides, a potentiator consisting of an aliphatic $C_2$–$C_{18}$-fatty acid, a mono-, di- or triglyceride of a $C_2$–$C_{12}$-fatty acid, a partial ester or complete ester of propylene glycol, polyethylene glycol or a carbohydrate with a $C_2$–$C_{12}$-fatty acid, a pharmaceutically compatible ester or ether thereof or of a mixutre of the said potentiators and, if desired, customary therapeutically inert adjuvants for suppositories, and their manufacture are described. These have valuable antimicrobial properties.

14 Claims, No Drawings

SUPPOSITORY DOSAGE FORM

DESCRIPTION OF THE INVENTION

The present invention is concerned with suppositories containing a therapeutically effective amount of ceftriaxone, a pharmaceutically compatible salt thereof or a hydrate of one of these compounds, a stabilizer consisting of a mono-, di- or triglyceride of a $C_{12}$–$C_{18}$-fatty acid or of a mixture of such glycerides, potentiator consisting of an aliphatic $C_2$–$C_{18}$-fatty acid, a mono-, di- or triglyceride of a $C_2$–$C_{12}$-fatty acid, a partial ester or complete ester of propylene glycol, polyethylene glycol or a carbohydrate with a $C_2$–$C_{12}$-fatty acid, a pharmaceutically compatible ester or ether thereof or of a mixture of the said potentiators and, if desired, customary therapeutically inert adjuvants for suppositories, and a process for their manufacture. These suppositories have valuable anti-microbial properties.

Cetriaxone, an antibiotic disclosed and claimed in U.S. Pat. No. 4,327,210, its pharmaceutically compatible salts and the hydrates of these compounds (referred to hereinafter as active substances) are relatively unstable compounds which change into inactive decomposition products upon lengthy storage, especially at room temperature and temperatures thereover. In the manufacture of pharmaceutical dosage forms this thermal lability is a difficult obstacle to overcome.

It has now surprisingly been found that the combination of the active substances with a mono-, di- or triglyceride of a $C_{12}$–$C_{18}$-fatty acid or a mixture of such glycerides brings about a considerable increase in the stability and storage capability of the active substances. This is all the more advantageous, as the combination of the active substance with the potentiator defined above often brings about an undesired reduction of the stability of the active substance. For example, this is the case when CAPMUL MCM 90 (a mixture of mono- and diglycerides of saturated $C_8$–$C_{10}$-fatty acids with 90% monoglyceride; Stokely-Van Camp Inc. Columbus, Ohio, USA) or CAPMUL 8210 (a similar composition to CAPMUL MCM 90, but with about 70% monoglycerides instead of 90%) is used as the potentiator.

The active substances are resorbed only slightly rectally. In order to increase the resorption the potentiator defined above is therefore used.

The triple combination described leads to stable preparations from which, moreover, the active substances are resorbed even better after rectal administration and is accordingly a valuable addition to medicinal resources.

Ceftriaxone disodium salt trihydrate is preferably used as the active substance. Preferred stabilizers are mixtures of mono-, di- and/or triglycerides of aliphatic $C_{12}$–$C_{18}$-fatty acids. Preferred potentiators are saturated $C_6$–$C_{12}$-fatty acids, unsaturated $C_{16}$–$C_{18}$-fatty acids, mono-, di- or triglycerides of $C_8$–$C_{12}$-fatty acids or mixtures thereof, edible oils containing these and mixtures thereof. Especially preferred potentiators are mixtures which contain predominantly mono- and di- glycerides of $C_8$–$C_{10}$-fatty acids, expecially of caprylic acid and capric acid. They preferably have a predominant amount of monoglyceride. The amount of monoglyceride preferably lies in a range of about 70% to about 90%.

The stabilizer is e.g. a mono-, di- or triglyceride of a straight-chain or branched-chain, saturated or unsaturated $C_{12}$–$C_{18}$-fatty acid. Examples of such fatty acids are lauric acid, myristic acid, palmitic acid, stearic acid, lauroleic acid (Δ9-dodecylenic acid), palmitoleic acid, oleic acid, ricinoleic acid, linoleic acid and linolenic acid. There is preferably used as the stabilizer a mixture of mono-, di- and/or triglycerides of $C_{12}$–$C_{18}$-fatty acids, which consists predominantly of the triglyceride of lauric acid ($C_{12}$).

The potentiator is e.g. a straight-chain or branched-chain, saturated or unsaturated $C_2$–$C_{18}$-fatty acid. Examples of such fatty acids are butyric acid, caproic acid, caprylic acid, capric acid, lauric acid, myristic acid, palmitic acid, stearic acid, lauroleic acid (Δ9-dodecylenic acid), palmitoleic acid, oleic acid, ricinoleic acid, linoleic acid and linolenic acid.

Under "fatty acids" there are to be understood saturated or unsaturated, monobasic aliphatic carboxylic acids which form esters with glycerine or other alcohols, whereby fats, oils, waxes and other lipids result.

The term "glycerides" relates to esters of glycerine, including the fats and oils, in which up to three molecules of fatty acid are bonded to one molecule of glycerine. Although the majority of glycerides with the same fatty acid are used, glycerides with different fatty acid residues also come into consideration. When glycerides with different fatty acid residues are used optically active compounds can occur.

As potentiators there also come into consideration the pharmaceutically compatible esters and ethers of the mentioned mono- and diglycerides and of the mentioned partial esters.

Suitable esterifying agents for the manufacture of the mentioned esters are, for example, those which are derived from pharmaceutically compatible weak acids such as tartaric acid and its diacetyl derivatives, acetic acid, ascorbic acid and citric acid or phosphoric acids with a monophosphate group which can form a monophosphate ester.

Suitable ethers can be formed by etherifying the free hydroxy group(s) with a reactive lower alkyl, alkenyl, alkynyl, aryl or substituted aryl compound, whereby the corresponding pharmaceutically compatible ether results. This reaction can be carried out in a manner known per se.

The suppositories in accordance with the invention preferably contain about 25 mg to about 2000 mg of ceftriaxone, especially about 50 mg to about 500 mg.

The active substance: stabilizer ratio in the suppositories in accordance with the invention conveniently varies between about 1:32 and about 1:1 and preferably lies between about 1:5 and about 1:1.5. The active substance: potentiator ratio conveniently lies between about 1:32 and about 1:0.2, preferably between about 1:16 and about 1:0.5.

The suppositories in accordance with the invention can also contain adjuvants which are known per se for the purpose of achieving a desired consistency. Further, they can contain water-soluble carriers such as polyethylene glycol, polypropylene glycol, glycerogelatine, methylcellulose or carboxymethylcellulose. There also come into consideration wetting agents, e.g. non-ionic wetting agents such as polyoxyethylene sorbitan fatty acid esters, polyoxyethylene sorbitol fatty acid esters, polyoxyethylene fatty acid esters, glycerine fatty acid esters as well as higher alcohol esters of polyoxyethylene, or anionic wetting agents such as esters of lower alkylsulphonic acids. Further, the suppositories can contain suitable emulsifying and dispersing agents, agents for adjusting the viscosity and colouring substances.

These suppositories can be manufactured in accordance with the invention by melting the stabilizer together with the potentiator by warming, homogeneously dispersing the active substance and, if desired, customary therapeutically inert adjuvants for suppositories in the melt obtained and formulating the dispersion obtained into suppositories of appropriate size using suppository moulds.

In order to demonstrate the increased stability of the suppositories in accordance with the invention compared with suppositories without a stabilzer, the suppository A described below was compared with suppository X described hereinafter:

| Suppository X | |
|---|---|
| Ceftriaxone disodium salt trihydrate (corresponding to 500 mg of ceftriaxone) | 596.5 mg |
| CAPMUL MCM90 | 500 mg |
| Gelatine (powder) | 160 mg |
| D-Mannitol (powder) | 25 mg |
| | 1281.5 mg |

This suppository is produced analogously to suppository A and is subsequently lyophilized.

TEST A

After storage for 10 months under the same conditions the suppositories A and X are tested for stability as follows:

A fixed portion is cut from each suppository. These portions are in each case dissolved at 40° C. in 3 ml of 100 percent dimethyl sulphoxide. After dilution with fixed amounts of water (corresponding to the standard curve for ceftriaxone: 0.125 μg/ml–4 μg/ml) the samples are investigated on the basis of microbiological "large plate analysis" in accordance with Analyst 80, 95, 110, 531 (1955). E. coli 1346 is used as the microorganism. The amount of ceftriaxone in the portions cut off is determined on the basis of the standard curve. The results are compiled in Table I.

TABLE I

| | Amount of ceftriaxone in the different portions | | | |
|---|---|---|---|---|
| | theoretical in mg | found in mg | in % | average in % |
| Suppository A | 24.8 | 25.4 | 102 | 98.8 |
| | 24.8 | 23.7 | 95.6 | |
| Suppository X | 64.3 | 54.4 | 84.6 | 77.4 |

TABLE I-continued

| Amount of ceftriaxone in the different portions | | | |
|---|---|---|---|
| theoretical in mg | found in mg | in % | average in % |
| 64.3 | 45.2 | 70.3 | |

TEST B

After storage for 12 months at 5° C. the suppositories A and X are tested for stability as follows by HPLC analysis:

A portion of the suppository A is dissolved in 1.0 ml of dimethyl sulphoxide while warming slightly. The solution is diluted to 50 ml with the freshly filtered mobile phase consisting of 4.0 g of tetraheptylammonium bromide, 500 ml of acetonitrile, 440 ml of water, 55 ml of phosphate buffer of pH 7.0 and 5 ml of citrate buffer of pH 5.0, filtered through a Miller HV filter (0.45 μm) and the solution obtained is analyzed by HPLC.

The suppository X is dissolved in 50 ml of the above mobile phase, and the solution obtained is filtered as above and analyzed by HPLC.

The results obtained are compiled in Table II hereinafter.

TABLE II

| | Amount of ceftriaxone determined in % |
|---|---|
| Suppository A | 94 |
| Suppository X | 51 |

The following comparison of the efficacy of the suppositories in accordance with the invention with conventional suppositories was investigated on the basis of single rectal administration of suppositories to human volunteers. There were used the already mentioned suppository A and a suppository Y which is identical with suppository X, but which in each case contains 300 mg of gelatine instead of 160 mg. These suppositories were administered successively to the same volunteers. The plasma levels of ceftriaxone were determined by analyses of blood samples, whereby the analytical method given in J. High Resolution Chromatographic Comm. No. 4, 1981, pp. 54–59 was used. The results are compiled in Table III. These show clearly that regularly higher blood levels of ceftriaxone in the blood are achieved with the suppository A in accordance with the invention than with the suppository Y which contains no stabilizer.

TABLE III

| | | Concentration of ceftriaxone in μg/ml plasma of human volunteers after single rectal administration of 500 mg of ceftriaxone | | | | | | | | | | |
|---|---|---|---|---|---|---|---|---|---|---|---|---|
| Volunteer | Suppository | 15 min. | 30 min. | 1 hr. | 1.5 hrs. | 2 hrs. | 3 hrs. | 4 hrs. | 5 hrs. | 6 hrs. | 8 hrs. | 10 hrs. | 24 hrs. |
| 1 | A | 3.78 | 12.53 | 11.54 | 10.37 | 9.34 | 8.61 | 7.22 | 5.93 | 4.41 | 4.27 | 3.44 | 1.04 |
| | Y | n.m.° | n.m. | n.m. | n.m. | n.m. | n.m. | n.m. | n.m. | n.m. | n.m. | n.m. | n.m. |
| 2 | A | 6.24 | 9.18 | 9.10 | 8.36 | 7.28 | 6.20 | 5.07 | 4.19 | 3.44 | 2.82 | 1.30 | n.m. |
| | Y | 1.96 | 3.78 | 5.28 | 4.19 | 3.95 | 3.28 | 2.83 | 2.44 | 2.03 | 1.54 | 1.32 | n.m. |
| 3 | A | 1.71 | 3.65 | 4.97 | 4.27 | 3.83 | 3.06 | 2.71 | 2.39 | 1.83 | 1.67 | 1.39 | n.m. |
| | Y | 2.06 | 6.09 | 4.66 | 4.57 | 4.30 | 3.41 | 3.23 | — | 2.15 | 1.88 | 1.34 | n.m. |
| 4 | A | 7.38 | 10.36 | 11.15 | 10.08 | 8.90 | 8.31 | 7.34 | 6.25 | 5.35 | 5.31 | 4.11 | 1.70 |
| | Y | 2.64 | 3.71 | 3.77 | 3.56 | 3.34 | 3.20 | 2.98 | 2.52 | 2.30 | 2.18 | 1.94 | 0.49 |
| 5 | A | 8.20 | 13.15 | 11.58 | 10.29 | 9.63 | — | 8.23 | 7.39 | 6.05 | 5.76 | 5.04 | 1.63 |
| | Y | 0.96 | 4.05 | 4.60 | 4.97 | 4.83 | 4.05 | 3.56 | 3.17 | 2.94 | 2.61 | 2.42 | 0.94 |
| 6 | A | 3.20 | 9.70 | 9.80 | 9.10 | 8.90 | 7.90 | 5.90 | 5.70 | 3.70 | 3.40 | 3.00 | n.m. |

TABLE III-continued

Concentration of ceftriaxone in μg/ml plasma of human volunteers after single rectal administration of 500 mg of ceftriaxone

| Volunteer | Suppository | 15 min. | 30 min. | 1 hr. | 1.5 hrs. | 2 hrs. | 3 hrs. | 4 hrs. | 5 hrs. | 6 hrs. | 8 hrs. | 10 hrs. | 24 hrs. |
|---|---|---|---|---|---|---|---|---|---|---|---|---|---|
| | Y | 3.46 | 5.21 | 8.89 | 8.76 | 8.07 | 7.04 | 6.15 | 5.41 | 4.89 | 4.05 | 3.41 | 0.96 |

*n.m. = not measurable

The following Example illustrates the present invention in more detail

EXAMPLE

| Suppository A: | |
|---|---|
| Ceftriaxone disodium salt trihydrate (corresponding to 500 mg of ceftriaxone) | 596.5 mg |
| CAPMUL MCM90 (a mixture of mono- and diglycerides of saturated $C_8/C_{10}$-fatty acids with 90% monoglyceride; Stokely-Van Camp Inc. Columbus, Ohio, USA) | 500 mg |
| Witepsol H15 (a mixture of mono-, di- and triglycerides of saturated $C_{12}$-$C_{18}$-fatty acids; Dynamit Nobel A.G., Germany) | 1303.5 mg |
| | 2400.0 mg |

The Witepsol is heated to 50° C. with the CAPMUL and melted. The melt is mixed with the active substance while stirring in order to obtain a homogeneous dispersion in the ground mass. The dispersion obtained is moulded into suppositories which have the weight given above.

Suppositories having the composition given in Table IV can be manufactured in an analogous manner.

TABLE IV

| | Amount in mg of | | | |
|---|---|---|---|---|
| | ceftriaxone* | CAPMUL MCM 90 | Witespol H15 | Weight of the suppository |
| Suppository B | 200 | 500 | 3300 | 4000 |
| Suppository C | 150 | 500 | 3350 | 4000 |
| Suppository D | 300 | 500 | 3200 | 4000 |
| Suppository E | 600 | 500 | 2900 | 4000 |
| Suppository F | 1200 | 500 | 2300 | 4000 |
| Suppository G | 600 | 1750 | 1650 | 4000 |
| Suppository H | 250 | 250 | 500 | 1000 |
| Suppository I | 500 | 500 | 1000 | 2000 |
| Suppository J | 1000 | 1000 | 2000 | 4000 |

*in the form of ceftriaxone disodium salt trihydrate.

What is claimed:

1. A suppository dosage form consisting essentially of a therapeutically effective amount of ceftriaxone, a pharmaceutically compatible salt thereof or a hydrate of one of these compounds, a stabilizer consisting of a mono-, di- or triglyceride of a $C_{12}$-$C_{18}$-fatty acid or of a mixture of such glycerides, a potentiator consisting of a mixture which contains mono- and diglycerides of $C_8$-$C_{10}$-fatty acids.

2. The suppository dosage form according to claim 1, wherein the active substance is ceftriaxone disodium salt trihydrate.

3. The suppository dosage form according to claim 1 or 2, wherein the stabilizer consists of a mixture of mono-, di- and/or triglycerides of $C_{12}$-$C_{18}$-fatty acids.

4. The suppository dosage form according to claim 3, wherein the stabilizer consists predominantly of the triglyceride of lauric acid ($C_{12}$).

5. The suppository dosage form according to claim 1, wherein the potentiator consists of a mixture which contains predominantly mono- and diglycerides of caprylic acid and capric acid.

6. The suppository dosage form according to claim 1, wherein the mixture of mono- and diglycerides has a predominant amount of monoglyceride.

7. The suppository dosage form according to claim 6, wherein the amount of monoglyceride amounts to about 70% to about 90%.

8. The suppository dosage form according to claim 1, wherein the amount of ceftriaxone amounts to about 25 mg to about 2000 mg.

9. The suppository dosage form according to claim 8, wherein the amount of ceftriaxone amounts to about 50 to about 500 mg.

10. The suppository dosage form according to claim 1, wherein the active substance: stabilizer ratio lies between about 1:32 and about 1:1.

11. The suppository dosage form according to claim 10, wherein the active substance: stabilizer ratio lies between about 1:5 and about 1:1.5.

12. The suppository dosage form according to claim 1, wherein the active substance: potentiator ratio lies between about 1:32 and about 1:0.2.

13. The suppository dosage form according to claim 12, wherein the active substance: potentiator ratio lies between about 1:16 and about 1:0.5.

14. The suppository dosage form according to claim 1, which contains therapeutically inert adjuvants for suppositories.

* * * * *